United States Patent [19]

Ross et al.

[11] Patent Number: 5,603,925
[45] Date of Patent: Feb. 18, 1997

[54] CLEAR OR TRANSLUCENT TACK-FREE ANTIPERSPIRANT STICK OR GEL COMPOSITION AND MANUFACTURING METHOD

[75] Inventors: Lloyd Ross, Hampton; Paul J. Fessock, South Plainfield, both of N.J.

[73] Assignee: The Mennen Company, Morristown, N.J.

[21] Appl. No.: 426,672

[22] Filed: Apr. 21, 1995

[51] Int. Cl.$^6$ .............................. A61K 7/32; A61K 7/38
[52] U.S. Cl. .................. 424/65; 424/68; 424/78.02; 424/78.05; 424/78.08; 424/78.31; 424/78.35; 514/946; 514/947; 528/310
[58] Field of Search ............... 424/65, 68, 400, 424/407, 401, 78.02, 78.05, 78.08, 78.31, 78.35; 528/310, DIG. 5; 514/946, 947

[56] References Cited

U.S. PATENT DOCUMENTS

| | | | |
|---|---|---|---|
| 3,148,125 | 9/1964 | Strianse et al. | 424/66 |
| 3,341,465 | 9/1967 | Kaufman et al. | 424/66 |
| 3,574,822 | 4/1971 | Shepherd et al. | 424/66 |
| 3,645,705 | 2/1972 | Miller et al. | 424/66 |
| 4,275,054 | 6/1981 | Sebag et al. | 424/66 |
| 4,383,988 | 5/1983 | Teng et al. | 424/66 |
| 4,425,327 | 1/1984 | Moller et al. | 424/65 |
| 4,673,570 | 6/1987 | Soldati | 424/66 |
| 4,822,603 | 4/1989 | Farris et al. | 424/66 |
| 4,863,721 | 9/1989 | Beck et al. | 424/47 |
| 4,919,934 | 4/1990 | Deckner et al. | 424/401 |
| 4,937,069 | 6/1990 | Shin | 424/66 |
| 4,944,937 | 7/1990 | McCall | 424/65 |
| 4,948,578 | 8/1990 | Burger et al. | 424/68 |
| 5,019,375 | 5/1991 | Tanner et al. | 424/66 |
| 5,069,897 | 12/1991 | Orr | 424/66 |
| 5,102,656 | 4/1992 | Kasat | 424/66 |

FOREIGN PATENT DOCUMENTS

| | | |
|---|---|---|
| 54-140714 | 4/1978 | Japan. |
| WO93/24105 | 12/1993 | WIPO. |

*Primary Examiner*—Terressa Mosley
*Attorney, Agent, or Firm*—Antonelli, Terry, Stout & Kraus, LLP

[57] ABSTRACT

Disclosed is a stick or gel composition, which can be clear or translucent, for combatting body malodor (e.g., an antiperspirant composition). The composition contains an antiperspirant active material (e.g., an antiperspirant active metal salt, such as aluminum chlorohydrate) and a polyamide gelling agent, and also contains a solvent system for the antiperspirant active material and polyamide, which dissolves the gelling agent and from which the gelling agent can be gelled. The solvent system is glycol-free, and includes a non-ionic surfactant (e.g., laureth-4) and a polar solvent (including water)). Use of the glycol-free solvent system achieves a gelled composition that has reduced levels of tack (is substantially tack-free) and has cosmetically acceptable properties. The composition can further include an opaque wax (e.g., stearyl alcohol), especially where the composition includes relatively small amounts of polyamide gelling agent, to provide additional structure and enhance dissolution of the polyamide gelling agent, while achieving a translucent composition which produces an optically clear film when applied to the skin. The composition containing the non-ionic surfactant and opaque wax can be processed, to form the gelled composition, at relatively low temperatures (180°–185° F.).

34 Claims, No Drawings

CLEAR OR TRANSLUCENT TACK-FREE ANTIPERSPIRANT STICK OR GEL COMPOSITION AND MANUFACTURING METHOD

BACKGROUND OF THE INVENTION

The present invention is directed to a clear or translucent composition, in gel or stick form, for combatting body malodor, the composition having an antiperspirant active ingredient incorporated therein. The composition of the present invention can be used to combat body malodor, e.g., in axillary regions of the human body, by applying the composition to the human body (for example, to the skin, in axillary regions of the body).

The present invention is particularly directed to clear or translucent antiperspirant compositions in stick or gel form. More particularly, the present invention is directed to a clear or translucent gel or stick composition including a polyamide gelling agent, and having an active ingredient (for example, an antiperspirant active material) incorporated therein, the polyamide gelling agent being stable even in the presence of acidic antiperspirant active materials. The present composition can, preferably, be translucent or clear, but need not be translucent or clear (that is, it can be opaque). Compositions according to the present invention can even be white-opaque as is conventional antiperspirant stick compositions which incorporate, for example, a waxy substance such as stearyl alcohol in the antiperspirant stick.

Antiperspirant products are well known in the art. Antiperspirant products have appeared in the marketplace in various dosage forms, such as sticks, gels, roll-ons, aerosols and creams. Generally, these dosage forms include a solution of the active ingredient in a suitable solvent, a suspension of the active ingredient in a non-solvent, or a multiphasic dispersion or emulsion in which a solution of the active ingredient is dispersed in some continuous phase or in which the solubilized active ingredient constitutes the continuous phase.

The stick form has become a dominant antiperspirant dosage form in the United States market, and is popular to varying degrees globally. Cosmetically acceptable antiperspirant sticks typically consist of a suspension of spray-dried antiperspirant active material in a vehicle such as cyclomethicone, with a waxy substance such as stearyl alcohol, alone or in combination with castor wax, gelling or thickening the suspension sufficiently to create a suitable stick.

The stick form can be distinguished from a gel or a paste in that in a stick, the formulated product can maintain its shape for extended time periods outside the package, the product not losing its shape significantly (allowing for some shrinkage due to solvent evaporation). One can adjust the amount of stearyl alcohol and castor wax and modify the manufacturing process to effect formation of a viscous gel or paste in place of the stick. Alternative gelling or thickening agents such as fumed silica can be used in place of the wax to form the gel or paste. These gels or pastes can be suitably packaged in containers which have the appearance of a stick, but which dispense through apertures on the top surface of the package. These products have been called soft sticks or "smooth-on". Hereinafter, these soft sticks are generically called "gels". Reference is made to U.S. Pat. No. 5,102,656 to Kasat, U.S. Pat. No. 5,069,897 to Orr, and U.S. Pat. No. 4,937,069 to Shin, each of which disclose such gels, including physical characteristics thereof such as viscosity and hardness. The contents of each of these three U.S. patents are incorporated herein by reference in their entirety.

The hard stick dosage form (hereinafter called "sticks"), although widely accepted by the consumer, suffers from leaving a white residue on skin after application, and can cause staining of fabric, which is considered to be undesirable, particularly by female consumers. The gel dosage form can be formulated to eliminate the white residue; however, the product appears initially as white and opaque, requiring consumer education and trial to fully appreciate the low-residue property. Furthermore, in gels of this type, the active ingredient is suspended in a vehicle such as cyclomethicone; in such suspensions, syneresis and creeping of the liquid is a common problem, resulting in instability of the formula or poor aesthetic properties, particularly when shipping product in warm climates and/or at high altitudes.

Recently, there has been significant activity in developing clear and translucent antiperspirant sticks and gels. Clear or translucent antiperspirant sticks consisting essentially of a solution of the active antiperspirant material in a polyhydric alcohol vehicle, gelled by dibenzylidene monosorbitol acetal, have been disclosed. Since the gelling agent is inherently unstable in an acidic environment, and since conventional antiperspirant active materials are acidic, much work has been involved in discovering suitable stabilizing or buffering agents to prevent or slow down acid attack on the acetal gelling agent. Such work has not been completely successful. Moreover, these clear or translucent antiperspirant sticks, containing the acetal gelling agent and including a solubilized antiperspirant active material, have the disadvantage of being inherently tacky. Development work in connection with these clear or translucent antiperspirant sticks, containing the acetal gelling agent, has focused on discovering suitable anti-tack agents for this dosage form. However, since acid hydrolysis of the gelling agent occurs more rapidly in aqueous solutions, formulators have been forced to avoid using water in the formulations. This severely restricts the ability of the formulator to develop cosmetically elegant formulations which are simultaneously chemically stable, optically clear, low in tack, low in residue and which have acceptable application aesthetics.

Clear and translucent antiperspirant gels (which have been dispensed from containers having the appearance of a stick) have been marketed, consisting of viscous, high internal phase emulsions. These gels exhibit some advantages over the aforementioned acetal-based clear sticks, in that the selection of formulation ingredients is less restricted (for example, water can be used), and often tack can be reduced significantly. But these emulsions still suffer from the disadvantages of feeling cool to the skin upon application, and often require the use of ethanol, which has negative environmental regulatory implications.

U.S. Pat. No. 5,500,209, naming as inventors the present inventors and others, discloses a gel or stick which includes active deodorant and/or antiperspirant ingredients, a polyamide gelling agent, and a solvent for the polyamide gelling agent, which gel or stick composition can be clear and/or translucent. The gelling agent is disclosed as forming a continuous phase of the composition, with the deodorant active and/or antiperspirant active ingredient in solution in this continuous phase, or dispersed in this continuous phase, or dissolved in a second, discontinuous phase which is emulsified in the continuous phase (forming a solid emulsion as the composition). This patent application discloses that the polyamide gelling agent is soluble in a cosmetically acceptable solvent at elevated temperatures, and solidifies (gels) upon cooling; acceptable solvents are disclosed as including various alcohols, including various glycols. An illustrative antiperspirant composition described in this aforementioned patent application contains the following:

(a) from 2 to 40 (preferably 6 to 20) weight percent, of the total weight of the composition, of a polyamide gellant, which is defined as a polymer that contains recurring amide groups as an integral part of the main chain;

(b) from 10 to 95 weight percent, preferably 30 to 95 weight percent, of the total weight of the composition, of a solvent for the polyamide gellant (this solvent can also serve as a cosmetic emollient);

(c) from 0 to 50 weight percent, preferably 0 to 25 weight percent, of the total weight of the composition, of a surface active agent to ensure rinsibility of the composition from the skin if the solvent is not sufficiently hydrophilic;

(d) from 4 to 30 weight percent, of the total weight of the composition, of an antiperspirant active ingredient; and (e) from 0–30 weight percent, of the total weight of the composition, of water.

The contents of U.S. Pat. No. 5,500,209, are incorporated herein by reference in their entirety.

While the polyamide-containing stick or gel disclosed in U.S. Pat No. 5,500,209 contains desirable properties in connection with stability of the composition, particularly in the presence of acidic antiperspirant active materials, and in providing clear or translucent gel or stick compositions, various attributes need to be improved. Specifically, the compositions according to U.S. Pat. No. 5,500,209, containing glycol solvents (e.g., propylene glycol) for the polyamide gelling agent and/or for the antiperspirant active material, have a disadvantageously large amount of tack. In addition, these compositions according to U.S. Pat. No. 5,500,209 containing glycol solvents, must be processed at relatively high temperatures (.for example, around 195° F.).

SUMMARY OF THE INVENTION

Accordingly, it is a first object of the present invention to provide a composition for combatting (reducing) body malodor, e.g., in stick or gel form, that can be opaque, translucent or clear, containing an antiperspirant active ingredient and, optionally, a deodorant active material, and containing a polyamide gelling agent, which has good pay-off and aesthetic characteristics, and which is substantially tack-free, and a method of forming such composition.

It is a further object of the present invention to provide a stick or gel composition for reducing body malodor, containing an antiperspirant active ingredient and a polyamide gelling agent, which composition has cosmetically acceptable characteristics, and a method of making such composition.

It is a further object of the present invention to provide an antiperspirant stick or gel composition containing a polyamide gelling agent, which is virtually tack-free, has cosmetically acceptable characteristics, and leaves an optically clear film on the skin, the antiperspirant stick or gel composition having good pay-off and application properties.

It is a still further object of the present invention to provide an antiperspirant stick or gel composition containing an antiperspirant metal salt such as aluminum chlorohydrate or aluminum-zirconium tetrachlorohydrex-Gly, and a polyamide gelling agent, which can be clear or translucent, which is substantially tack-free with cosmetically acceptable characteristics, which produces an optically clear film when applied to skin, and which has good pay-off and application properties.

It is a still further object of the present invention to provide a method of forming a stick or gel composition for reducing body malodor, such as an antiperspirant stick or gel composition, containing an antiperspirant active ingredient and polyamide gelling agent, which can be manufactured at lower processing temperatures.

The foregoing objects are achieved by the composition according to the present invention, containing (1) an antiperspirant active material and (2) a polyamide gelling agent, and further containing (3) a solvent system for the antiperspirant active material and the polyamide, with the solvent system for the antiperspirant active material and for the polyamide gelling agent being glycol-free and containing a non-ionic surfactant and a polar solvent, the polar solvent including water. In general, the polyamide gelling agent dissolves in the non-ionic surfactant. Water is the polar solvent, and with the non-ionic surfactant acts as a dispersing medium for the antiperspirant active material, in which sufficient water is used to give a clear or translucent solution/ emulsion of the antiperspirant active material.

The gelling agent is included in an sufficient amount such that the composition can be solidified, and the solvent system is provided in an amount such that the polyamide can be dissolved therein and the polyamide can be gelled therefrom. Of course, the antiperspirant active material is included in the composition in an amount effective to reduce body malodor.

Glycol solvent for a polyamide gelling agent and/or for an antiperspirant active material (even where the glycol solvent is complexed with the antiperspirant active material (e.g., antiperspirant metal salt), and the antiperspirant active material itself, contribute to the undesirable tack. By avoiding use of the glycol solvent, tack is reduced so as to provide a virtually tack-free composition. By utilizing the glycol-free composition, a virtually tack-free composition can be achieved.

Additional advantages of the present invention can be achieved by including an opaque wax, such as stearyl alcohol and/or methyl 12-hydroxystearate, in the composition. The opaque wax (e.g., stearyl alcohol) is included in the solvent system. The opaque wax is soluble in the non-ionic surfactant (e.g., laureth-4), and enhances the solubility of the polyamide gelling agent in the non-ionic surfactant (more generally, in the solvent system). The opaque wax also lowers the temperature at which the polyamide gelling agent dissolves in the solvent system. The opaque wax also provides additional structure to the composition, particularly where the composition contains relatively small amounts of the polyamide gelling agent (for example, where the sticks contain 7% by weight, of the total weight of the composition, of the polyamide gelling agent). Incorporating relatively small amounts of the opaque wax, as compared to the amount of nonionic surfactant incorporated in the composition, surprisingly increases the translucency of the sticks (that is, provides a stick that is relatively clearer, as compared to the same stick not containing the opaque wax), notwithstanding that the wax is opaque, and produces a composition that provides an optically clear film when applied to the skin.

The foregoing objectives are also achieved upon utilizing such glycol-free solvent system, including the opaque wax, with the components being heated and mixed at temperatures of at most 185° F. (for example, 180°–185° F.) when forming the gelled composition.

Accordingly, through use of the present invention, utilizing a glycol-free solvent system (that is, wherein neither the solvent for the antiperspirant active material or the solvent for the polyamide gelling agent is a glycol), the solvent system containing a polar solvent including water and a non-ionic surfactant, a clear or translucent antiperspirant gel or stick can be achieved which is substantially tack-free and has cosmetically acceptable characteristics, leaves an optically clear film on the skin, and has good pay-off and application properties. Moreover, by additionally including an opaque wax in the solvent system, structure and properties of the composition are further improved, and the gelled composition can be fabricated at lower temperatures.

DETAILED DESCRIPTION OF THE INVENTION

While the present invention will be described in connection with specific and preferred embodiments, it will be understood that it is not intended to limit the invention to those embodiments. To the contrary, it is intended to cover all alterations, modifications and equivalents as may be included within the spirit and scope of the invention as defined by the appended claims.

Throughout the present disclosure, the present invention is described primarily in connection with an antiperspirant composition, including clear and translucent antiperspirant gel and stick compositions. However, the present invention is not limited to such compositions; for example, the composition according to the present invention can be a deodorant composition. Moreover, depending on additional active ingredients included in the composition, the composition can also be an emollient composition, a sunscreen composition, etc. As to the various types of cosmetic sticks and active materials incorporated therein, which is applicable to the present invention, attention is directed to U.S. Pat. No. 4,322,400 to Yuhas, the contents of which are incorporated herein by reference in their entirety.

Throughout the present specification, "deodorant active" materials and "antiperspirant active" materials are discussed. Both types of materials contributed to reduction of body (for example, axillary) malodor. By reduction of body malodor, we mean that, generally, there is less body malodor after application of the composition to a person's skin, as compared to body malodor of the person without application of the composition. Such reduction can be due to a masking of the malodor, absorption and/or chemical reaction of the malodorous materials, reduction of levels of the bacteria producing the malodorous materials, e.g., from perspiration, reduction of perspiration, etc. The antiperspirant materials, when utilized in appropriate amounts, primarily act to reduce body malodor by reducing production of perspiration; the antiperspirant materials can also have a deodorant function, e.g., as an antimicrobial agent. The deodorant active materials do not substantially reduce the production of perspiration, but reduce malodor in other ways, e.g., as fragrances masking the malodor or reducing the malodor intensity, as odor adsorbents, as antimicrobial agents, as agents chemically reacting with malodorous materials, etc.

Throughout the present specification, where compositions are described as including or comprising specific components or materials, it is contemplated by the inventors that the compositions of the present invention also consist essentially of, or consist of, the recited components or materials. Accordingly, throughout the present disclosure any described composition of the present invention can consist essentially of, or consist of, the recited components or materials.

As indicated previously, a desired feature of the present invention is that a clear, or at least a translucent, antiperspirant stick or gel composition, can be provided. The term clear or transparent (that is, clarity), according to the present invention, is intended to connote its usual dictionary definition; thus, a clear antiperspirant stick allows ready viewing of objects behind it. By contrast, a translucent antiperspirant stick, although allowing light to pass through, causes the light to be so scattered that it will be impossible to see clearly objects behind the translucent stick. Opaque compositions do not allow a substantial amount of light to pass therethrough.

Within the context of the present invention, a stick or gel (e.g., an antiperspirant stick or gel) is deemed to be transparent or clear if the maximum transmittance of light of any wavelength in the range 400 to 800 nm through a sample 1 cm thick is at least 35%, preferably at least 50%. The stick or gel is deemed translucent if the maximum transmittance of such light through the sample is between 2% and less than 35%. A stick or gel is deemed opaque if the maximum transmittance of light is less than 2%. The transmittance can be measured by placing a sample of the aforementioned thickness into a light beam of a spectrophotometer whose working range includes the visible spectrum, such as a Bausch & Lomb Spectronic 88 Spectrophotometer. As to this definition of clear, see European Patent Application Publication No. 291,334A2.

The present invention contemplates a gel or a stick composition, for reducing body malodor, using polyamide as the gelling agent and including an antiperspirant active material, the antiperspirant active material and gelling agent being in a glycol-free solvent system for the polyamide gelling agent and for the antiperspirant active material, the solvent system being included in an amount in which the polyamide can be dissolved and from which the polyamide can solidify and form a gelled composition. This glycol-free solvent system includes a non-ionic surface active agent (in which the polyamide gelling agent can be dissolved) and a polar solvent (the polar solvent including water). The composition can also include a deodorant active material, such as a deodorant fragrance and/or an antimicrobial agent; the composition should include the deodorant active material in sufficient amounts so that after application to the skin malodor is reduced (this includes wherein a desired fragrance is increased).

As a further aspect of the present invention, the composition also contains an opaque wax. The wax can be a low melting point wax or a high melting point wax, but preferably is a low melting point wax. The opaque wax is soluble in the non-ionic surfactant, enhances solubility of the polyamide gelling agent in the non-ionic surfactant, and lowers the temperature at which the polyamide dissolves in the solvent system. The amount of opaque wax incorporated in the composition is dependent on the amount of non-ionic surfactant therein; a ratio of amount of non-ionic surfactant to the amount of opaque wax should be such that an optically clear film is produced on the skin when the composition is rubbed on the skin.

The opaque wax also provides additional structure to the composition, particularly where the polyamide gelling agent is included in the composition in relatively small amounts (e.g., 7% by weight, of the total weight of the composition). Thus, by including the opaque wax, a stick composition (rather than a gel) can be formed even where the composition contains relatively small amounts of the polyamide gelling agent, which stick composition can be at least translucent and produce an optically clear film on the skin.

Illustratively (and not limiting), for a given amount of non-ionic surfactant in the composition, applicants have surprisingly found that when including opaque waxes such as stearyl alcohol or methyl 12-hydroxystearate in the composition, in amounts of 5% by weight, of the total weight of the composition, or less than 5%, the composition becomes more translucent (less opaque) and produces an optically clear film when applied to the skin, notwithstanding that the wax is opaque.

Through use of the glycol-free solvent system containing the opaque wax, together with the water and the non-ionic surfactant, lower processing temperatures for forming the gelled composition can be used. For example, in previously proposed compositions utilizing a glycol-containing (for example, propylene glycol-containing) solvent system, processing at 195° F., to form the gelled composition, is necessary. According to the present invention, lower processing temperatures for forming the mixture of components to be gelled (that is, temperatures less than 185° F., e.g., 180°–185° F.) can be utilized.

Conventional antiperspirant metal salts can be incorporated in the composition of the present invention, as the antiperspirant active material. See U.S. Pat. No. 5,500,209 the contents of which has previously been incorporated herein by reference in their entirety, for a description of antiperspirant active materials (e.g., antiperspirant metal salts) which can be incorporated in the composition of the present invention. The polyamide gelling agent, as part of the gelled composition, is stable in an acidic environment, so that the stability of the composition according to the present invention, in the presence of conventional acidic antiperspirant metal salts, is excellent.

Various antiperspirant active materials, which may be mentioned by way of example (and not of a limiting nature), including aluminum chlorohydrate, aluminum chloride, aluminum sesquichlorohydrate, zirconyl hydroxychloride, aluminum-zirconium hydroxychlorides, aluminum-zirconium glycine complex (e.g., aluminum-zirconium tetrachlorohydrex-Gly), etc., can be utilized as the antiperspirant active material in the composition of the present invention. Generally, Category I active antiperspirant ingredients listed in the Food and Drug Administration's Monograph on Antiperspirant Drug Products for Over-The-Counter Human Use (Oct. 10, 1993) can be used. In addition, any new drug, not listed in the Monograph, such as aluminum nitratohydrate and its combination with zirconyl hydroxychlorides and nitrates, or aluminum-stannous chlorohydrates, can be incorporated as an antiperspirant active ingredient in antiperspirant compositions according to the present invention.

It must be noted that, as a commercial product, various antiperspirant metal salts come in a solution of propylene glycol. Such solutions cannot be incorporated as part of the present invention, since such would not provide a glycol-free solvent system.

The antiperspirant active material illustratively can be included in the composition in amounts up to 30% by weight, preferably 20–22% by weight, of the total weight of the composition. As an illustrative minimum amount, and not to be limiting, the composition could include at least 0.1% by weight antiperspirant active material, of the total weight of the composition; however, at low amounts the material may not reduce perspiration (e.g., may act as a deodorant active material, such as an antimicrobial agent).

The polyamide gellant will be further described in the following. For a more specific description of polyamides which can be incorporated as the gelling agent in the present invention, attention is directed to the disclosure of the polyamide gelling agent in the aforementioned U.S. Pat. No. 5,500,209, the contents of which have previously been incorporated herein by reference in their entirety.

Polyamides, in general, are polymers that contain recurring amide groups as integral parts of the main polymer chain. Typically, linear polyamides are formed from the condensation reaction of amino acid bifunctional monomers, or, alternatively, from the condensation of dibasic acids and diamines. Dicarboxylic acids fall within the dibasic acids which can be utilized for forming polyamides by condensation with diamines. The polyamide should be soluble in the solvent system at, e.g., elevated temperatures. Because of this, it is preferred that the polyamides are not extensively crosslinked covalently (which would prevent solubility).

Many conventional polyamides, such as nylon 6, do not exhibit adequate solubility in the solvents of interest, and are not preferred. There are two classes of polyamides which possess enhanced solubility, and are particularly preferred as polyamides for use in the present invention: (1) those based on terpolymers of simple nylons (such as DuPont Elvamide 8061 which is a terpolymer of nylon 6, nylon 66 and nylon 610); and (2) polyamides based on complex fatty acids (such as the Versamid series of Henkel Corp. or the Uni-Rez series of Union Camp Corp.). This latter class of polyamides is formed by condensation of (1) diamines with (2) relatively high molecular weight polybasic acids or esters, including dibasic acids or esters, which are obtained from thermal polymerization of a diene acid or ester, such as linoleic acid (for example, linoleates from soy bean, cotton seed or corn oils). The dibasic or polybasic acids are normally mixtures of materials. Typically, the largest component is a dibasic dimeric fatty acid possessing 18 carbon atoms per carboxyl group, but other mono- or polybasic fractions may be present. These polyamides are also called fatty polyamides, or polyamides from long-chain fatty acids (and esters). The fatty acids employed as reagents are typically derived from tall oil, and illustratively (but not limiting) include oleic, linoleic and arachadonic acid.

Neutral polyamides are preferred as gelling agents according to the present invention. Neutral polyamides based on dimer acids, and preferred for use in the present invention, generally have molecular weights from 1,000 to 30,000 daltons (molecular weight can be determined by gel permeation chromatography (GPC), with tetrahydrofuran (THF) a typical solvent).

Examples of commercial polyamides which can be used as the polyamide gelling agent in the composition of the present invention are "Versamid" 1655 (by Henkel Corporation, CAS 68915-56-0), "Versamid" 744 (by Henkel Corporation, CAS 67989-30-4), "Uni-Rez" 2931 (by Union Camp Corporation, CAS 68139-80-0), "Macromelt" 6212 (by Henkel Corporation, CAS 68650-50-0) and "Versamid" 930 (by Henkel Corporation, CAS 32131-17-2). Other commercial polyamides which can be used as the polyamide gelling agent include "Uni-Rez" 2658, "Uni-Rez" 2970, "Uni-Rez" 2621, "Uni-Rez" 2613, "Uni-Rez" 2624, "Uni-Rez" 2665, "Uni-Rez" 1554, "Uni-Rez" 2623, "Uni-Rez" 2662, "Versamid" 1655 and "Versamid" 744. The "Uni-Rez" polyamides are by Union Camp Corp., and the "Versamid" polyamides are by Henkel Corp.

The polyamide is included in the composition in a sufficient amount such that the gelling agent as a whole gels and solidifies the composition to form a solid having a hardness of a gel or stick. Generally, lesser amounts of polyamide, without further gelling or thickening agents, will provide a gel composition, while increased amounts of the polyamide (or including co-gellants or thickeners with the polyamide)

can provide stick compositions. Illustratively, the polyamide is included in the composition in an amount of 2–40% by weight, of the total weight of the composition (preferably 5–13% by weight, of the total weight of the composition).

According to the present invention, the solvent system, for dissolving both the polyamide and for dissolving the antiperspirant active material (for example, an antiperspirant active metal salt or salts, or complex containing such salt or salts) is to be free of glycol (for example, free of propylene glycol) and must contain a non-ionic surface active agent and a polar solvent (water). Illustrative of the non-ionic surfactant is laureth-4 (which is a polyethylene glycol ether of lauryl alcohol, containing four ethylene oxide units). Other alkoxylated alcohols, either straight or branched chain, saturated or unsaturated, can also be utilized as the nonionic surfactant. For example, ethoxylated and/or propoxylated fatty alcohols, having 1–20 ethylene oxide and/or propylene oxide units, and wherein the fatty alcohol has a carbon chain length within the range of $C_8$–$C_{20}$, can be utilized as the non-ionic surfactant. The non-ionic surfactant illustratively can be included in the composition in an amount of 5–30% by weight, of the total weight of the composition. The preferred non-ionic surfactant is the aforementioned laureth-4. Oleth-3, Oleth-5, Isosteareth-2 and Isosteareth-10 are non-ionic surfactants that can be incorporated in the compositions according to the present invention.

Water is an essential ingredient of the present composition. The water, as a polar solvent, is used (in combination with the non-ionic surfactant) as a dispersing medium for the antiperspirant active material, and is included in the composition in sufficient amount to provide a clear or translucent solution/emulsion of the antiperspirant active material (e.g., antiperspirant active metal salt). Illustratively, and not of a limiting nature, the water is included in the composition in an amount up to 25% by weight, of the total weight of the composition. The amount of water is adjusted based on the amount of the antiperspirant active material; that is, the more antiperspirant active material, the more water is needed. In addition to dissolving the antiperspirant active material, the water gives a smooth feel to the stick, and also provides clarity.

Desirably, and particularly where relatively small amounts of polyamide gelling agent are included in the composition, the solvent system of the composition also includes an opaque wax. An illustrative, and preferred opaque wax is stearyl alcohol. However, the present invention is not limited to use of stearyl alcohol as the opaque wax. Other low melting point waxes, including other fatty alcohols, can be utilized as the opaque wax. Illustratively, the fatty alcohols have a carbon chain length within the range of $C_8$–$C_{30}$, preferably within the range of $C_{12}$–$C_{18}$, most preferably stearyl alcohol (a carbon chain length of $C_{18}$). Another low melting point opaque wax is methyl 12-hydroxystearate. Optionally, high melting point opaque waxes can be utilized for at least part of the low melting point wax referred to previously. Such high melting point opaque waxes are known and include beeswax, spermaceti, castor wax, etc., and have a function of the low melting point wax.

Where the composition contains both the non-ionic surfactant and the opaque wax, it is preferred that the weight ratio of non-ionic surfactant to the opaque wax is within the range of 1:1 to 5:1; more preferably, the weight ratio of non-ionic surfactant to opaque wax is 3:1. Within this range, surprisingly the translucency of the composition increases (that is, the composition is clearer, notwithstanding that the composition contains an opaque wax), and the composition produces an optically clear film when applied to the skin.

Illustratively, the opaque wax is included in the composition in an amount of 5% or less by weight, of the total weight of the composition. Of course, where an opaque or less translucent stick is acceptable, the composition can include more opaque wax, either high-melting-point and/or low-melting-point wax.

The solvent system, as a whole, is included in the composition in an amount of 5%–70% by weight, preferably 5%–15% by weight, of the total weight of the composition.

The compositions according to the present invention can contain, but need not contain, volatile silicone. Omission of the silicone provides greater translucency (more clarity), but reduces cosmetic properties.

The composition according to the present invention can include other ingredients conventionally incorporated in deodorant or antiperspirant gels and/or sticks, particularly if clarity is not a factor. As for various other ingredients which can be incorporated, attention is directed to the optional components such as hardeners, strengtheners, chelating agents, colorants, perfumes, emulsifiers and fillers, described in various patent documents listed in the following, all incorporated by reference herein in their entirety:

U.S. Pat. No. 3,255,082 to Barton;

U.S. Pat. No. 4,049,792 to Elsnau;

U.S. Pat. No. 4,137,306 to Rubino, et al; and

U.S. Pat. No. 4,279,658 to Hooper, et al.

Again, attention is directed to U.S. patent application Ser. No. 08/214,111, filed Mar. 17, 1994, the contents of which have previously been incorporated herein by reference in their entirety, for various optional components, and amounts thereof, which can be incorporated in the composition of the present invention.

Appropriate deodorant active materials can be incorporated in the compositions of the present invention, so as to provide deodorant active materials combatting body malodor. For example, a fragrance and/or antimicrobial agent can be incorporated. A fragrance would, illustratively, be included in an amount of 0.5%–3.0% by weight, of the total weight of the composition; the antimicrobial agent, such as Triclosan, would preferably be included in an amount of from 0.1% to 0.5% by weight, of the total weight of the composition.

The degree of freedom in incorporating optional ingredients is increased, where a clear composition is not being formed (for example, where a translucent composition, or, especially, where an opaque compositions, is being formed).

Compositions according to the present invention can be made by mixing the various components at an elevated temperature (that is, by heating and mixing the various components) and then cooling in order to form the gelled (solidified) composition (as a gel or stick). Desirably, any volatile components (such as fragrances) are added to the mixture at a relatively late stage of the mixing, so as to limit volatilization of the volatile components. Generally, the solvent and polyamide gelling agent are mixed and heated so as to fully dissolve the polyamide in the solvent. An active ingredient (for example, antiperspirant active material, e.g., in dry form or as part of a water or non-glycol-containing solution) can be added after the polyamide fully dissolves, and mixing then takes place. Mixing continues with cooling, with, for example, color and fragrance then being added. Thereafter, the resulting composition, still liquid, is poured into canisters, e.g., dispensing packages, and solidified, as with conventional stick and gel compositions.

According to one aspect of the present invention, and due to use of the solvent system which is free of glycol and which contains the non-ionic surfactant, water and the opaque wax, the elevated temperature at which the various components are mixed (that is, the elevated temperature to which the various components are heated, for mixing) can be lower than that when the solvent includes, e.g., propylene glycol. Thus, according to the present invention, the components need not be heated above 185° F., as the elevated temperature at which mixing takes place. Accordingly, due to this aspect of the present invention, energy costs (for heating) can be reduced, and volatilization of volatile components can also be reduced, providing additional advantages for the present invention.

The compositions according to the present invention are used in the same manner as conventional gel or stick compositions, dispensed from, for example, dispensing canisters. For example, the gel or stick, exposed out of the dispensing package, is rubbed on skin, so as to deposit the active material (e.g., antiperspirant and/or deodorant active materials) on the skin. Illustratively, where the composition is an antiperspirant composition containing an antiperspirant active material for reducing perspiration in the axillary regions, an exposed portion of the composition is rubbed against axillary regions of the human body, so as to deposit the antiperspirant active material and, if present, deodorant active material, on the skin in the axillary regions. As set forth previously, the gel or stick according to the present invention has good pay-off properties, so as to deposit sufficient antiperspirant active material (and, if present, sufficient deodorant active material) on the skin. Moreover, the compositions according to the present invention are substantially tack-free with good pay-off and application properties, and have cosmetically acceptable characteristics.

In the following, specific examples of compositions within the scope of the present invention are set forth. Of course, these specific examples are illustrative of the present invention, and are not limiting. In these examples, which are clear antiperspirant sticks, the amounts of the components are in weight percent, of the total weight of the composition. In the following examples, as well as throughout the present specification, various names utilized are the CTFA (Cosmetics, Toiletry and Fragrance Association, Inc.) names, as set forth in the CTFA International Cosmetic Ingredient Dictionary (4th Ed. 1991).

| Component | Wt % |
|---|---|
| EXAMPLE I | |
| Deionized Water | 12.50 |
| Laureth-4 | 10.00 |
| DEA Oleth-1-Phosphate | 1.00 |
| Myreth-2-Octanoate | 3.00 |
| Tridecyl Neopentanoate | 19.00 |
| Polyamide | 6.00 |
| Stearyl Alcohol | 5.00 |
| Methyl 12-Hydroxystearate | 3.00 |
| Ethylene Dioleamide | 2.00 |
| Silicon Dioxide | 1.00 |
| Cyclomethicone (Pentamer) | 16.35 |
| Silicone-5 Cs. | 2.00 |
| Aluminum/Zirconium Tetrachlorohydrex—Gly | 18.00 |
| Fragrance | 1.00 |
| Color | 0.15 |
| Total Materials | 100.00 |
| EXAMPLE II | |
| PPG-2 Myristyl Ether Propionate | 20.88 |
| Cyclomethicone (Pentamer) | 18.50 |
| Aluminum/Zirconium Tetrachlorohydrex—Gly | 18.00 |
| Deionized Water | 12.50 |
| Laureth-4 | 8.00 |
| Polyamide | 7.00 |
| Methyl 12-Hydroxystearate | 4.00 |
| Stearyl Alcohol | 3.00 |
| Nonoxynol-9 | 2.00 |
| Ethylene Dioleamide | 2.00 |
| Silicone - 50 Cs. | 2.00 |
| Silicon Dioxide | 1.00 |
| Fragrance | 1.00 |
| Color | 0.12 |
| Total Materials | 100.00 |
| EXAMPLE III | |
| Aluminum/Zirconium Tetrachlorohydrex Gly | 22.00 |
| PPG-2 Myristyl Ether Propionate | 20.93 |
| Water | 18.00 |
| Cyclomethicone | 8.50 |
| Laureth-4 | 8.00 |
| Polyamide | 7.00 |
| Methyl 12-hydroxystearate | 4.00 |
| Stearyl Alcohol | 3.00 |
| PEG-40 Hydrogenated Castor Oil | 2.00 |
| Ethylene Dioleamide | 2.00 |
| Dimethicone | 1.00 |
| Ceteareth-10 | 1.00 |
| Silica | 0.25 |
| Dimethylpolysiloxane | 0.20 |
| Perfume and Color | q.s. |
| Total Materials | 100.00 |
| EXAMPLE IV | |
| Aluminum/Zirconium Tetrachlorohydrex Gly | 18.00 |
| PPG-2 Myristyl Ether Propionate | 17.19 |
| Water | 12.50 |
| Cyclomethicone | 4.00 |
| Laureth-4 | 8.00 |
| Polyamide | 7.00 |
| Stearyl Alcohol | 6.00 |
| Paraffin Wax | 4.00 |
| Nonoxynol-9 | 2.00 |
| Dimethicone | 2.00 |
| Silica | 1.00 |
| Perfume and Color | q.s. |
| Total Materials | 100.00 |
| EXAMPLE V | |
| Aluminum/Zirconium Tetrachlorohydrex Gly | 18.00 |
| Water | 12.50 |
| Cyclomethicone | 18.50 |
| Laureth-4 | 8.00 |
| Polyamide | 6.00 |
| Methyl 12-hydroxystearate | 2.00 |
| Stearyl Alcohol | 5.00 |
| Nonoxynol-9 | 3.00 |
| Phenyl Trimethicone | 1.00 |
| Myreth-3-Octanoate | 3.00 |
| Oleth-10 Phosphate | 1.00 |
| Cyclomethicone (and) Dimethicone Copolyol | 2.00 |
| Tridecyl Neopentannate | 12.00 |
| Hydrogenated Castor Oil | 4.00 |
| Ethylene Dioleamide | 2.00 |
| Silica | 1.00 |
| Perfume and Color | q.s. |
| Total Materials | 100.00 |
| EXAMPLE VI | |
| PPG-2 Myristyl Ether Propionate | 20.93 |
| Cyclomethicone (Pentamer) | 8.50 |
| Aluminum/Zirconium Tetrachlorohydrex—Gly | 22.00 |
| Deionized Water | 18.00 |
| Laureth-4 | 8.00 |
| Polyamide | 7.00 |
| Methyl 12-Hydroxystearate | 4.00 |
| Stearyl Alcohol | 3.00 |

-continued

| Component | Wt % |
| --- | --- |
| PEG-40 Hydrogenated Castor Oil | 2.00 |
| Ethylene Dioleamide | 2.00 |
| Silicone-50 cs | 2.00 |
| Silicon Dioxide | 0.25 |
| Dimethyl Polysiloxane | 0.20 |
| Ceteareth-10 | 1.00 |
| Fragrance | 1.00 |
| Color | 0.12 |
| Total Materials | 100.00 |

EXAMPLE VII

| Component | Wt % |
| --- | --- |
| PPG-2 Myristyl Ether Propionate | 20.66 |
| Cyclomethicone (Pentamer) | 13.00 |
| Aluminum/Zirconium Tetrachlorohydrex—Gly | 22.00 |
| Deionized Water | 15.00 |
| Laureth-4 | 8.00 |
| Polyamide | 7.00 |
| Methyl 12-Hydroxystearate | 2.12 |
| Stearyl Alcohol | 2.50 |
| PEG-40 Hydrogenated Castor Oil | 1.50 |
| Ethylene Dioleamide | 1.80 |
| Silicone-50 cs | 1.80 |
| Talc | 0.50 |
| C18–38 Hydroxylstearylstearate | 1.00 |
| Hydrogenated Castor Oil | 2.00 |
| Fragrance | 1.00 |
| Color | 0.12 |
| Total Materials | 100.00 |

Thus, according to the present invention, a stick or gel composition, which is clear or translucent, containing an antiperspirant active material and a polyamide gelling agent and having good pay-off and application properties, while being substantially tack-free and having cosmetically acceptable properties, can be achieved. These compositions leave an optically clear film on the skin. These compositions are stable, even in the presence of conventional acidic antiperspirant metal salts, such as aluminum chlorohydrate or aluminum-zirconium tetrachlorohydrex-Gly. In addition, the compositions according to the present invention can be formed at relatively low temperatures, and have low (or no) residue characteristics.

While we have shown and described several embodiments in accordance with the present invention, it is understood that the same is not limited thereto, but is susceptible to numerous changes and modifications as known to one having ordinary skill in the art, and we therefore do not wish to be limited to the details shown and described herein, but intend to cover all such modifications as are encompassed by the scope of the appended claims.

We claim:

1. A composition for reducing body malodor, comprising:

(1) an antiperspirant active material, in an amount effective to reduce body malodor;

(2) a polyamide as a gelling agent for the composition, the gelling agent being included in a sufficient amount such that the composition can be solidified; and (3) a solvent system for the antiperspirant active material and for the polyamide, the solvent system being glycol-free and including a non-ionic surfactant and a polar solvent, the polar solvent including water, the solvent system being provided in an amount such that the polyamide can be dissolved therein and the polyamide can be gelled therefrom.

2. The composition according to claim 1, wherein the antiperspirant active material includes antiperspirant active metal salts.

3. The composition according to claim 2, wherein the antiperspirant active metal salts include aluminum-zirconium glycine complex.

4. The composition according to claim 2, wherein the antiperspirant active metal salts are included in the composition in an amount sufficient to reduce flow of body perspiration, whereby the composition is an antiperspirant composition.

5. The composition according to claim 1, further including an opaque wax.

6. The composition according to claim 5, wherein the opaque wax is included in the composition such that a weight ratio of the non-ionic surfactant to the opaque wax is in a range of 1:1 to 5:1.

7. The composition according to claim 6, wherein the opaque wax is a fatty alcohol having a carbon chain length in the range of $C_8$–$C_{30}$.

8. The composition according to claim 7, wherein the fatty alcohol is stearyl alcohol.

9. The composition according to claim 8, wherein the non-ionic surfactant is an alkoxylated fatty alcohol, having 1–20 alkylene oxide units.

10. The composition according to claim 9, wherein the composition includes 5–30% by weight of the alkoxylated fatty alcohol, of the total weight of the composition.

11. The composition according to claim 10, wherein the alkoxylated fatty alcohol is laureth-4.

12. The composition according to claim 10, wherein the alkoxylated fatty alcohol is selected from the group consisting of ethoxylated and propoxylated fatty alcohols.

13. The composition according to claim 5, wherein the opaque wax includes a low melting point wax.

14. The composition according to claim 13, wherein the opaque wax also includes a high melting point wax.

15. The composition according to claim 5, wherein the opaque wax is methyl 12-hydroxystearate.

16. The composition according to claim 5, wherein the composition includes, in % by weight of the total weight of the composition, up to 30% by weight of the antiperspirant active material, 2%–40% by weight of the polyamide, and 5%–70% of the solvent system.

17. The composition according to claim 16, wherein water is included in the composition in an amount up to 25% by weight, of the total weight of the composition.

18. The composition according to claim 17, wherein the polyamide is included in the composition in an amount in a range of 5%–13% by weight, of the total weight of the composition.

19. The composition according to claim 17, wherein the non-ionic surfactant is included in the composition in an amount of 5%–30% by weight, of the total weight of the composition, and wherein a weight ratio of the non-ionic surfactant to the opaque wax is in a range of 1:1 to 5:1.

20. The composition according to claim 19, wherein the non-ionic surfactant is an alkoxylated fatty alcohol.

21. The composition according to claim 1, wherein the water is provided in a sufficient amount so as to provide a translucent or clear solution or emulsion of the antiperspirant active material in the composition.

22. The composition according to claim 1, further including a volatile silicone.

23. The composition according to claim 1, which is a translucent composition.

24. The composition according to claim 1, which is a clear composition.

25. The composition according to claim 1, which is a gel.

26. The composition according to claim 1, which is a solid stick.

27. A composition for reducing body malodor, comprising:
- (a) an antiperspirant active metal salt, in an amount of 0.1%–30% by weight, of the total weight of the composition;
- (b) a polyamide as a gelling agent of the composition, in an amount of 2%–40% by weight, of the total weight of the composition;
- (c) water, in an amount from a minimum amount sufficient to dissolve the antiperspirant active metal salt, and up to 25% by weight, of the total weight of the composition; and
- (d) an non-ionic surfactant, in an amount of 5%–30% by weight, of the total weight of the composition, the composition being glycol-free.

28. The composition according to claim 27, wherein the composition further comprises an opaque wax, and wherein a weight ratio of non-ionic surfactant to opaque wax, in the composition, is from 1:1 to 5:1.

29. The composition according to claim 28, wherein the opaque wax is stearyl alcohol.

30. The composition according to claim 29, wherein the non-ionic surfactant is laureth-4.

31. A method of forming a gelled composition for reducing body malodor, comprising the steps of heating and mixing a polyamide gelling agent, an antiperspirant active material, a non-ionic surfactant, a polar solvent, the polar solvent including water, and an opaque wax, so as to form a mixture, the mixture being glycol-free, the heating being performed such that the mixture is a liquid and is at a maximum temperature of 185° F., and cooling the mixture so as to gel the mixture, thereby forming the gelled composition.

32. The method according to claim 31, wherein the nonionic surfactant is laureth-4.

33. The method according to claim 32, wherein the opaque wax is stearyl alcohol.

34. The composition according to claim 1, wherein the composition is free of tack.

* * * * *